United States Patent
Wong et al.

(10) Patent No.: US 11,434,189 B1
(45) Date of Patent: Sep. 6, 2022

(54) METHOD FOR ISOLATING CURCUMINOIDS FROM TURMERIC RHIZOME

(71) Applicants: I-MEI FOODS CO., LTD., Taipei (TW); Chi-Ming Kao, Taipei (TW)

(72) Inventors: Ken-Pei Wong, Taipei (TW); Ya-Chi Tsai, Taipei (TW)

(73) Assignees: I-MEI FOODS CO., LTD., Taipei (TW); Chi-Ming Kao, Taipei (TW)

( * ) Notice: Subject to any disclaimer, the term of this patent is extended or adjusted under 35 U.S.C. 154(b) by 0 days.

(21) Appl. No.: 17/505,775

(22) Filed: Oct. 20, 2021

(51) Int. Cl.
*C07C 45/82* (2006.01)
*C07C 45/79* (2006.01)
*C07C 45/81* (2006.01)
*B01D 11/02* (2006.01)
*B01D 9/00* (2006.01)

(52) U.S. Cl.
CPC ............ *C07C 45/79* (2013.01); *B01D 9/0063* (2013.01); *B01D 11/0203* (2013.01); *B01D 11/0288* (2013.01); *C07C 45/81* (2013.01); *B01D 2009/0086* (2013.01)

(58) Field of Classification Search
CPC ...... C07C 45/79; C07C 45/81; B01D 11/0288
See application file for complete search history.

(56) References Cited

U.S. PATENT DOCUMENTS

| | | | |
|---|---|---|---|
| 5,679,864 A * | 10/1997 | Krackov | C07C 49/248 568/313 |
| 2010/0098788 A1* | 4/2010 | Alberte | A61K 36/9066 514/683 |
| 2016/0256513 A1 | 9/2016 | May et al. | |

FOREIGN PATENT DOCUMENTS

| | | |
|---|---|---|
| CN | 1150924 | 6/1997 |
| CN | 1566215 A | 1/2005 |
| CN | 101585757 A | 11/2009 |
| CN | 102617316 | 8/2012 |
| CN | 105669410 B | 5/2018 |
| CN | 108339086 A | 7/2018 |
| TW | 201019949 A | 6/2010 |
| TW | 201345541 A | 11/2013 |
| WO | 2021021014 A1 | 2/2021 |

OTHER PUBLICATIONS

Search Report appended to an Office Action, which was issued to Taiwanese counterpart application No. 109124604 by the TIPO dated Mar. 9, 2021, with an English translation thereof.
Search Report, issued to European counterpart application No. 21203597.6 by the EPO, dated May 10, 2022 (7 pages).

* cited by examiner

*Primary Examiner* — Sikarl A Witherspoon
(74) *Attorney, Agent, or Firm* — Hamre, Schumann, Mueller & Larson, P.C.

(57) ABSTRACT

A method for isolating curcuminoids from turmeric rhizome includes the steps of a) subjecting the turmeric rhizome to extraction with a first ethanol solution having an ethanol concentration ranging from 90% to 100% at a stirring speed ranging from 100 rpm to 300 rpm so as to obtain an ethanol-extracted product; and b) subjecting the ethanol-extracted product to crystallization with a second ethanol solution having an ethanol concentration ranging from 90% to 100 at a temperature ranging from 2° C. to 8° C. and a stirring speed ranging from 40 rpm to 300 rpm so as to obtain the curcuminoids.

13 Claims, No Drawings

METHOD FOR ISOLATING CURCUMINOIDS FROM TURMERIC RHIZOME

FIELD

The disclosure relates to a method for isolating curcuminoids, and more particularly to a method for isolating curcuminoids from turmeric rhizome.

BACKGROUND

Turmeric (*Curcuma longa* L.) is a perennial plant of genus *Curcuma* in the ginger family (Zingiberaceae), and is usually 1 to 1.5 meters tall. Turmeric roots are stout with dilated tuberous ends. Turmeric leaves are oblong or elliptic with short tapering tips. Turmeric bracts are ovate or oblong with blunt tips, and are light green. Turmeric corolla is yellowish. Turmeric is mainly distributed in southeastern India, Jamaica, China, Bangladesh, Caribbean, South America, etc.

The main useful part of turmeric is rhizome thereof. In folk medicine, turmeric has effects of stimulating blood circulation and relieving menstrual pain. In addition, it has been reported that curcuminoids (i.e., one of the main active ingredients of turmeric, including curcumin, bisdemethoxycurcumin, and demethoxycurcumin) exerts a variety of beneficial effects on human bodies, including antioxidant, anti-inflammatory, antiviral, antibacterial, antifungal, and anticancer effects. Therefore, mass production of curcuminoids has become a major research focus for those skilled in the art.

The conventional methods for producing curcumin include extraction with various organic solvents (e.g., acetone or isopropanol) and hydrolysis with acidic and/or alkaline solvents (see, e.g., CN 102617316 B and CN 1566215 A). However, use of these solvents can be harmful to environment or human health. In addition, extraction efficiency of some solvents is poor. Therefore, multiple extractions or further use of ultrasonic extraction and supercritical fluid extraction are required to improve curcuminoid yield (see, e.g., CN 105669410 B and CN 1150924 C), which is not only cumbersome and time consuming, but also increases the cost required for practical application in the industry.

Therefore, it is desirable to develop a method for producing curcuminoids with a high yield, a simple operation procedure, and a low cost.

SUMMARY

Therefore, an object of the disclosure is to provide a method for efficiently isolating curcuminoids from turmeric rhizome using a simple process.

According to the disclosure, there is provided a method for isolating curcuminoids from turmeric rhizome. The method includes the steps of:

a) subjecting the turmeric rhizome to extraction with a first ethanol solution having an ethanol concentration ranging from 90% to 100% at a stirring speed ranging from 100 rpm to 300 rpm so as to obtain an ethanol-extracted product; and b) subjecting the ethanol-extracted product to crystallization with a second ethanol solution having an ethanol concentration ranging from 90s to 100% at a temperature ranging from 2° C. to 8° C. and a stirring speed ranging from 40 rpm to 300 rpm so as to obtain the curcuminoids.

DETAILED DESCRIPTION

A method for isolating curcuminoids from turmeric rhizome according to the disclosure includes the steps of:

a) subjecting the turmeric rhizome to extraction with a first ethanol solution having an ethanol concentration ranging from 90% to 100% at a stirring speed ranging from 100 rpm to 300 rpm so as to obtain an ethanol-extracted product; and b) subjecting the ethanol-extracted product to crystallization with a second ethanol solution having an ethanol concentration ranging from 90% to 100% at a temperature ranging from 2° C. to 8° C. and a stirring speed ranging from 40 rpm to 300 rpm so as to obtain the curcuminoids.

In some embodiments of the disclosure, in step a), the extraction is performed with the first ethanol solution having the ethanol concentration of 95% at the stirring speed of 280 rpm.

In some embodiments of the disclosure, in step b), the crystallization is performed with the second ethanol solution having the ethanol concentration of 95% at the temperature of 4° C. and the stirring speed of 60 rpm.

Various turmeric cultivars can be used in the method of the disclosure. In some embodiments of the disclosure, the turmeric cultivars include red turmeric, yellow turmeric, *Curcuma zedoaria* (also known as white turmeric), *Curcuma xanthorrhiza* (also known as Java turmeric), and combinations thereof. In an exemplary embodiment of the disclosure, the turmeric cultivar is red turmeric.

In some embodiments of the disclosure, in step a), the first ethanol solution is present in an amount ranging from 5 mL per gram to 10 mL per gram of the turmeric rhizome. In an exemplary embodiment of the disclosure, in step a), the first ethanol solution is present in an amount of 5 mL per gram of the turmeric rhizome.

In some embodiments of the disclosure, in step a), the extraction is performed at a temperature ranging from 10° C. to 100° C. for a time period ranging from 15 minutes to 150 minutes. In an exemplary embodiment of the disclosure, in step a), the extraction is performed at a temperature of 25° C. for a time period of 30 minutes.

In some embodiments of the disclosure, in step b), the second ethanol solution is present in an amount ranging from 1 g per gram to 20 g per gram of the ethanol-extracted product.

In some embodiments of the disclosure, in step b), the crystallization is performed at the temperature ranging from 3° C. to 6° C. for the time period ranging from 12 hours to 72 hours. In an exemplary embodiment of the disclosure, in step b), the crystallization is performed at the temperature of 4° C. for the time period of 24 hours.

In some embodiments of the disclosure, the curcuminoids include curcumin, bisdemethoxycurcumin, demethoxycurcumin, or combinations thereof. In an exemplary embodiment of the disclosure, the curcuminoids include a combination of curcumin, bisdemethoxycurcumin, and demethoxycurcumin.

In some embodiments, the first ethanol solution used in step a) is a recycled ethanol solution obtained from the extraction, and the method of the disclosure further includes the steps of leaving the ethanol-extracted product to stand at a temperature ranging from −20° C. to 8° C. for a time period of 24 hours prior to step b), and sieving the curcuminoids through a sieve of from 20 mesh to 100 mesh after step b).

In some embodiments, the method of the disclosure further includes, prior to step a), subjecting the turmeric rhizome to lyophilization for a time period ranging from 12 hours to 48 hours. Specifically, the lyophilization is performed by freezing the turmeric rhizome after washing with deionized water to a temperature ranging from −20° C. to −10° C., followed by drying the turmeric rhizome at a first raised temperature ranging from 30° C. to 40° C. for a first time period ranging from 3 hours to 6 hours and then at a second raised temperature ranging from 50° C. to 60° C. for a second time period ranging from 18 hours to 21 hours.

Examples of the disclosure will be described hereinafter. It is to be understood that these examples are exemplary and explanatory and should not be construed as a limitation to the disclosure.

EXAMPLES

General Experimental Materials

1. Preparation of Turmeric Rhizome Powder

Turmeric rhizome powder used in following examples was prepared by washing fresh red turmeric rhizome purchased from Zuojhen District, Tainan City, Taiwan with deionized water, followed by lyophilization for 24 hours, grinding using a grinder (Manufacturer: Hsiang Tai Machinery Industry Co., Ltd.; Model: SM-3C), and sieving using a sieve with an aperture of 0.18 mm.

General Experimental Procedures

1. Quantitative Analysis of Curcuminoids

In the following examples, contents of curcuminoids (including curcumin, bisdemethoxycurcumin, and demethoxycurcumin) in each test sample were determined by reference to a method described in "Method of Test for Curcuminoids in Foods in Capsule and Tablet Form" published by the Ministry of Health and Welfare, Taiwan on Mar. 19, 2015, and by performing an ultra performance liquid chromatography (UPLC) analysis using an ACQUITY UPLC® photodiode array (PDA) eλ detector from Waters Corporation. The operating conditions for performing the UPLC analysis are shown in Table 1 below.

TABLE 1

Operating conditions for UPLC analysis

| Operating conditions | Details |
|---|---|
| Type of chromatograhy column | Acclaim C30 3 μm column |
| Size of chromatograhy column | 2.1 mm × 15 cm |
| Temperature of chromatography column | 35° C. |
| Detection wavelength | 420 nm |
| Mobile phase | 2% acetic acid solution/acetonitrile, 60/40 (v/v) |
| Flow rate | 0.4 mL/min |
| Injection volumn of test sample | 5 μL |

In addition, for comparison, proper amounts of curcumin, bisdemethoxycurcumin, and demethoxycurcumin purchased from Sigma-Aldrich were respectively dissolved in 100% methanol to prepare curcumin, bisdemethoxycurcumin and demethoxycurcumin solutions with concentrations ranging from 0.1 μg/mL to 20 μg/mL as control standards, and then subjected to the UPLC analysis.

The total curcuminoid content was calculated by adding up the contents of curcumin, bisdemethoxycurcumin, and demethoxycurcumin.

Example 1: Preparation of Ethanol-Extracted Products of Turmeric (*Curcuma longa* L.) Rhizomes A. Effects of Different Extraction Methods on Total Curcuminoid Content:

Turmeric rhizome powder prepared in section 1 of the General Experimental Materials was divided into one experimental group (i.e., Experimental group 1) and two comparative experimental groups (i.e., Comparative experimental groups 1 and 2), and then subjected to extraction processes shown in Table 2 below.

The extraction process for the turmeric rhizome powder of Experimental group 1 was performed according to the following steps: First, 30 g of the turmeric rhizome powder was added with 150 mL of 95% ethanol and mixed thoroughly. Then, extraction was performed at a temperature of 25° C. and a stirring speed of 280 rpm for a time period of 30 minutes.

Extraction process for the turmeric rhizome powder of Comparative experimental group 1 was performed according to the following steps. First, 30 g of the turmeric rhizome powder was added with 150 mL of 95% ethanol and mixed thoroughly. Then, ultrasonic extraction was performed at a temperature of 25° C. for a time period of 30 minutes using an ultrasonicator (purchased from Taiwan Supercritical Technologies Co., Ltd., Model: ES-600N) at a frequency of 25 KHz to 30 KHz.

Extraction process for the turmeric rhizome powder of Comparative experiment group 2 was performed according to the following steps. First, 30 g of the turmeric rhizome powder was placed in an extraction vessel of a supercritical fluid extraction system (purchased from Taiwan Supercritical Technologies Co., Ltd., Model: OV-SCF-B). Then, supercritical $CO_2$ was introduced into the extraction vessel and 95% ethanol was added as a co-solvent. After that, supercritical fluid extraction was performed at a temperature of 40° C. and a pressure of 4350 psi for a time period of 30 minutes.

A 250 mesh filter screen was then used to filter each of ethanol-extracted semi-products of Experimental group 1 and Comparative experimental groups 1 and 2 so as to collect each of filtrates of Experimental group 1 and Comparative experimental groups 1 and 2. Ethanol contained in each of the filtrates was removed by a concentration process under reduced pressure to obtain an ethanol-extracted product of the turmeric rhizome of each of Experimental group 1 and Comparative experimental groups 1 and 2.

TABLE 2

Extraction processes

| Groups | Extraction processes |
|---|---|
| Experimental group 1 | Stirring extraction (25° C., 280 rpm) |
| Comparative experimental group 1 | Ultrasonic extraction (25° C., 25-30 KHz) |
| Comparative experimental group 2 | Supercritical fluid extraction (40° C., 4350 psi) |

Thereafter, 10 mg to 20 mg of the ethanol-extracted product of the turmeric rhizome of each of Experimental group 1 and Comparative experimental groups 1 and 2 was mixed in 10 mL of methanol to prepare a test sample. The curcuminoid content in the test sample of each of Experimental group 1 and Comparative experimental groups 1 and 2 was analyzed according to the procedures described in section 1 of the General Experimental Procedures. The results are shown in Table 3 below.

TABLE 3

| Total curcuminoid contents | |
| --- | --- |
| Groups | Total curcuminoid contents (wt %) |
| Experimental group 1 | 48.65 |
| Comparative experimental group 1 | 35.55 |
| Comparative experimental group 2 | 37.99 |

As shown in Table 3, the total curcuminoid content in Experimental group 1 is significantly higher than those in Comparative experimental groups 1 and 2. These results show that the total curcuminoid content in the ethanol-extracted product of the turmeric rhizome obtained by the stirring extraction at a stirring speed of 280 rpm is significantly higher than those obtained by the ultrasonic extraction and the supercritical fluid extraction.

B. Effects of Various Concentrations of Extracting Solvents on Total Curcuminoid Contents:

The turmeric rhizome powder was divided into one experimental group (i.e., Experimental Group 1) and two comparative experimental groups (i.e., Comparative experimental groups 1 and 2). The turmeric rhizome powder of Experimental group 1 was subjected to the stirring extraction in accordance with the procedures described for Experimental group 1 in the abovementioned section A. The turmeric rhizome powder of each of Comparative experimental groups 1 and 2 was also subjected to the similar procedures as described for Experimental group 1 in the abovementioned section A, except that 50% ethanol and 75% ethanol were used in Comparative experimental groups 1 and 2, respectively, to replace 95% ethanol.

Thereafter, the ethanol-extracted product of the turmeric rhizome of each of Experimental group 1 and Comparative experimental groups was prepared into a test sample as described in the abovementioned section A. The total curcuminoid content in the test sample of each of Experiment group 1 and Comparative experimental groups 1 and 2 was analyzed according to the procedures as described in section 1 of the General Experimental Procedures. The results are shown in Table 4 below.

TABLE 4

| Total curcuminoid contents | |
| --- | --- |
| Groups | Total curcuminoid contents (wt %) |
| Experimental group 1 | 42.60 |
| Comparative experimental group 1 | 7.29 |
| Comparative experimental group 2 | 24.20 |

As shown in Table 4, the total curcuminoid content in Experimental group 1 is significantly higher than those in Comparative experimental groups 1 and 2. These results show that the total curcuminoid content in the ethanol-extracted product of the turmeric rhizome obtained by the stirring extraction using 95% ethanol is significantly higher than those obtained by the stirring extractions using 50% ethanol and 75% ethanol.

Example 2: Purification of Curcuminoids in Ethanol-Extracted Product of Turmeric Rhizome by Crystallization To evaluate the effect of various crystallization conditions on purification of curcuminoids (including curcumin, bis-demethoxycurcumin, and demethoxycurcumin) from the ethanol-extracted product of the turmeric rhizome, the following experiments were performed.

Experimental Procedures

The ethanol-extracted product of the turmeric rhizome of Experimental group 1 as described in the abovementioned section A of Example 1 was divided into one experimental group (i.e., Experimental group 1) and two comparative experimental groups (i.e., Comparative experimental groups 1 and 2). The ethanol-extracted product of the turmeric rhizome of each of Experimental group 1 and Comparative experimental groups 1 and 2 was subjected to a crystallization process at 4° C. with the conditions shown in Table 5 below.

TABLE 5

| Crystallization conditions | | |
| --- | --- | --- |
| | Crystallization conditions | |
| Groups | Solvents | Stirring speeds (rpm) |
| Experimental group 1 | Ethanol | 60 |
| Comparative experimental group 1 | Ethanol | — |
| Comparative experimental group 2 | Isopropanol | 60 |

Specifically, the crystallization process for Experimental group 1 was performed according to the following steps. First, 3 g of the ethanol-extracted product of the turmeric rhizome was added with 5 g of 95% ethanol and mixed thoroughly, followed by continuously stirring at a temperature of 4° C. and a stirring speed of 60 rpm for a time period of 24 hours, and then left to stand at a temperature of 4° C. for a time period of 24 hours to form a precipitate. The precipitate was collected by filtration and dried in an oven at a temperature set to 60° C.

The crystallization process for Comparative experimental group 1 was performed using the steps substantially the same as those described above for Experimental group 1, except that stirring was not performed.

The crystallization process for Comparative experimental group 2 was performed using the steps substantially the same as those described above for Experimental group 1, except that isopropanol was used to replace ethanol.

Thereafter, 10 mg to 20 mg of the precipitate of each of Experimental group 1 and Comparative experimental groups 1 and 2 was taken mixed in 10 ml of methanol to prepare a test sample. The total curcuminoid content in the test sample of each of Experimental group 1 and Comparative experimental groups 1 and 2 was analyzed according to the procedures described in section 1 of the General Experimental Procedures. The results are shown in Table 6 below.

Results:

TABLE 6

| Total curcuminoid contents | |
|---|---|
| Groups | Total curcuminoid contents (wt %) |
| Experimental group 1 | 95.92 |
| Comparative experimental group 1 | 88.41 |
| Comparative experimental group 2 | 74.28 |

As shown in Table 6, the total curcuminoid content in Experimental group 1 is significantly higher than those measured in Comparative experimental groups 1 and 2. These results show that curcuminoids with a higher purity can be obtained by crystallizing the ethanol-extracted product of the turmeric rhizome using ethanol at a low temperature with stirring during the crystallization process.

Example 3: Use of a Recycled Ethanol Solution for Preparation of Ethanol-Extracted Products of Turmeric Rhizomes The turmeric rhizome powder was divided into one experimental group (i.e., Experimental Group 1) and two comparative experimental groups (i.e., Comparative experimental groups 1 and 2). The turmeric rhizome powder of Experimental group 1 was subjected to the stirring extraction in accordance with the procedures described for Experimental group 1 in the abovementioned section A of Example 1 except that a recycled 90% ethanol obtained from a previous extraction process was used to replace 95% ethanol. A concentrate obtained by the concentration process was left to stand at a temperature of from 2° C. to 8° C. for a time period of 24 hours to form a precipitate (an oleoresin).

The precipitate was subjected to the crystallization process in accordance with the procedures described for Experimental group 1 in Example 2. The curcuminoids obtained by the crystallization process was sieved through a sieve of from 20 mesh to 100 mesh.

The turmeric rhizome powder of Comparative experimental group 1 was used to isolate the curcuminoids in accordance with the processes substantially the same as those described above for Experimental group 1, except that the curcuminoids obtained by the crystallization process was not sieved.

The turmeric rhizome powder of Comparative experimental group 2 was used to isolate the curcuminoids in accordance with the processes substantially the same as those described above for Experimental group 1, except that the concentrate obtained by the concentration process was not left to stand and the curcuminoids obtained by the crystallization process was not sieved.

Preparation of the test sample of each of Experimental group 1 and Comparative experimental groups 1 and 2 was performed according to the procedures described in the section entitled "Experimental Procedures" of Example 2. The total curcuminoid content in the test sample of each of Experimental group 1 and Comparative experimental groups 1 and 2 was analyzed according to the procedures described in section 1 of the General Experimental Procedures. The results are shown in Table 7 below.

Results:

TABLE 7

| Total curcuminoid contents | |
|---|---|
| Groups | Total curcuminoid contents (wt %) |
| Experimental group 1 | 100.00 |
| Comparative experimental group 1 | 93.31 |
| Comparative experimental group 2 | 88.14 |

As shown in Table 7, the total curcuminoid content in Experimental group 1 is significantly higher than those measured in Comparative experimental groups 1 and 2. These results show that when a recycled ethanol solution is used for the extraction process, curcuminoids with a higher purity can be obtained by leaving the concentrate obtained by the concentration process to stand for a time period prior to the crystallization process and sieving the curcuminoids obtained by the crystallization process.

Example 4: Compositional Analysis of the Curcuminoids

Experimental Procedures:

The turmeric rhizome powder was subjected to stirring extraction according to the procedures described for Experimental group 1 in section A of Example 1. Crystallization of the ethanol-extracted product of the turmeric rhizome and preparation of the test sample were performed according to the procedures described for Experimental group 1 in the section entitled "Experimental Procedures" of Example 2. Thereafter, contents of curcumin, bisdemethoxycurcumin, and demethoxycurcumin in the test samples were analyzed according to the procedures described in section 1 of the General Experimental Procedures, and the total curcuminoid content was further calculated. The experiments were repeated three times, and the obtained data were expressed as mean±standard deviation (S.D.).

The results are shown in Table 8 below.

Results:

TABLE 8

| Curcuminoid contents | |
|---|---|
| Curcumin content (wt %) | 84.45 ± 1.03 |
| Bisdemethoxycurcumin content (wt %) | 1.45 ± 0.07 |
| Demethoxycurcumin content (wt %) | 12.04 ± 1.55 |
| Total curcuminoid content (wt %) | 97.94 ± 1.1 |

As shown in Table 8, it is possible to obtain a product containing three different types of curcuminoids, in which the content of curcumin is the highest.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for isolating curcuminoids from turmeric rhizome, comprising the steps of:
   a) subjecting the turmeric rhizome to extraction with a first ethanol solution having an ethanol concentration ranging from 90% to 100% at a stirring speed ranging from 100 rpm to 300 rpm so as to obtain an ethanol-extracted product; and
   b) subjecting the ethanol-extracted product to crystallization with a second ethanol solution having an ethanol concentration ranging from 90% to 100% at a temperature ranging from 2° C. to 8° C. and a stirring speed ranging from 40 rpm to 300 rpm so as to obtain the curcuminoids.

2. The method according to claim 1, wherein in step a), the first ethanol solution is present in an amount ranging from 5 mL per gram to 10 mL per gram of the turmeric rhizome.

3. The method according to claim 1, wherein in step a), the extraction is performed at a temperature ranging from 10° C. to 100° C. for a time period ranging from 15 minutes to 150 minutes.

4. The method according to claim 1, wherein in step b), the second ethanol solution is present in an amount ranging from 1 g per gram to 20 g per gram of the ethanol-extracted product.

5. The method according to claim 1, wherein in step b), the crystallization is performed at the temperature ranging from 3° C. to 6° C. for a time period ranging from 12 hours to 72 hours.

6. The method according to claim 1, wherein the curcuminoids include curcumin, bisdemethoxycurcumin, demethoxycurcumin, or combinations thereof.

7. The method according to claim 1, further comprising, prior to step a), subjecting the turmeric rhizome to lyophilization for a time period ranging from 12 hours to 48 hours.

8. The method according to claim 7, wherein the lyophilization includes freezing the turmeric rhizome to a temperature ranging from −20° C. to −10° C., and drying the turmeric rhizome at a first raised temperature ranging from 30° C. to 40° C. for a first time period ranging from 3 hours to 6 hours and at a second raised temperature ranging from 50° C. to 60° C. for a second time period ranging from 18 hours to 21 hours.

9. The method according to claim 1, wherein in step a), the extraction is performed with the first ethanol solution having the ethanol concentration of 95% at the stirring speed of 280 rpm.

10. The method according to claim 1, wherein in step a), the first ethanol solution is a recycled ethanol solution.

11. The method according to claim 10, further comprising leaving the ethanol-extracted product to stand at a temperature ranging from −20° C. to 8° C. for a time period of 24 hours prior to step b).

12. The method according to claim 10, further comprising sieving the curcuminoids through a sieve of from 20 mesh to 100 mesh after step b).

13. The method according to claim 11, further comprising sieving the curcuminoids through a sieve of from 20 mesh to 100 mesh after step b).

* * * * *